United States Patent [19]

Rispeter

[11] Patent Number: 5,336,268
[45] Date of Patent: Aug. 9, 1994

[54] ADJUSTABLE HIP JOINT ENDOPROSTHESIS

[75] Inventor: Siegfried Rispeter, Besigheim, Fed. Rep. of Germany

[73] Assignee: Dr. Ing. h.c.F. Porsche AG, Fed. Rep. of Germany

[21] Appl. No.: 991,347

[22] Filed: Dec. 15, 1992

[30] Foreign Application Priority Data

Dec. 17, 1991 [DE] Fed. Rep. of Germany ....... 4141527

[51] Int. Cl.⁵ ............................................... A61F 2/34
[52] U.S. Cl. ............................................ 623/23; 623/18
[58] Field of Search ..................... 623/16, 18, 22, 23

[56] References Cited

U.S. PATENT DOCUMENTS

| | | | |
|---|---|---|---|
| 3,067,740 | 12/1962 | Haboush | 623/23 |
| 4,115,875 | 9/1978 | Rambert et al. | 623/23 |
| 4,129,903 | 12/1978 | Hggler | 623/23 |
| 4,963,155 | 10/1990 | Lazzeri et al. | 623/23 |
| 5,002,578 | 3/1991 | Luman | 623/23 |
| 5,002,581 | 3/1991 | Paxson | 623/23 |
| 5,211,666 | 5/1993 | Fetto | 623/23 |

FOREIGN PATENT DOCUMENTS

| | | |
|---|---|---|
| 0000549 | 2/1979 | European Pat. Off. . |
| 0038897 | 11/1981 | European Pat. Off. ............. 623/23 |
| 0190981 | 3/1986 | European Pat. Off. . |
| 0339530 | 11/1989 | European Pat. Off. . |
| 0428303 | 5/1991 | European Pat. Off. . |
| 2605514 | 4/1988 | France . |

*Primary Examiner*—David Isabella
*Attorney, Agent, or Firm*—Evenson, McKeown, Edwards & Lenahan

[57] ABSTRACT

An adjustable hip joint endoprosthesis has an adjustable prosthesis head, which is connected with a stem that can be fixed in the femur. To absorb overloads, which would result in damage to the prosthesis part implanted into the femur and therefore in another implantation, a limiting element is provided. This limiting element is arranged in the prosthesis head and absorbs the overload by deformation, fracture or, in the case of a frictionally engaged connection, by sliding. After the occurrence of an overload, the limiting element must be replaced or re-adjusted.

5 Claims, 1 Drawing Sheet

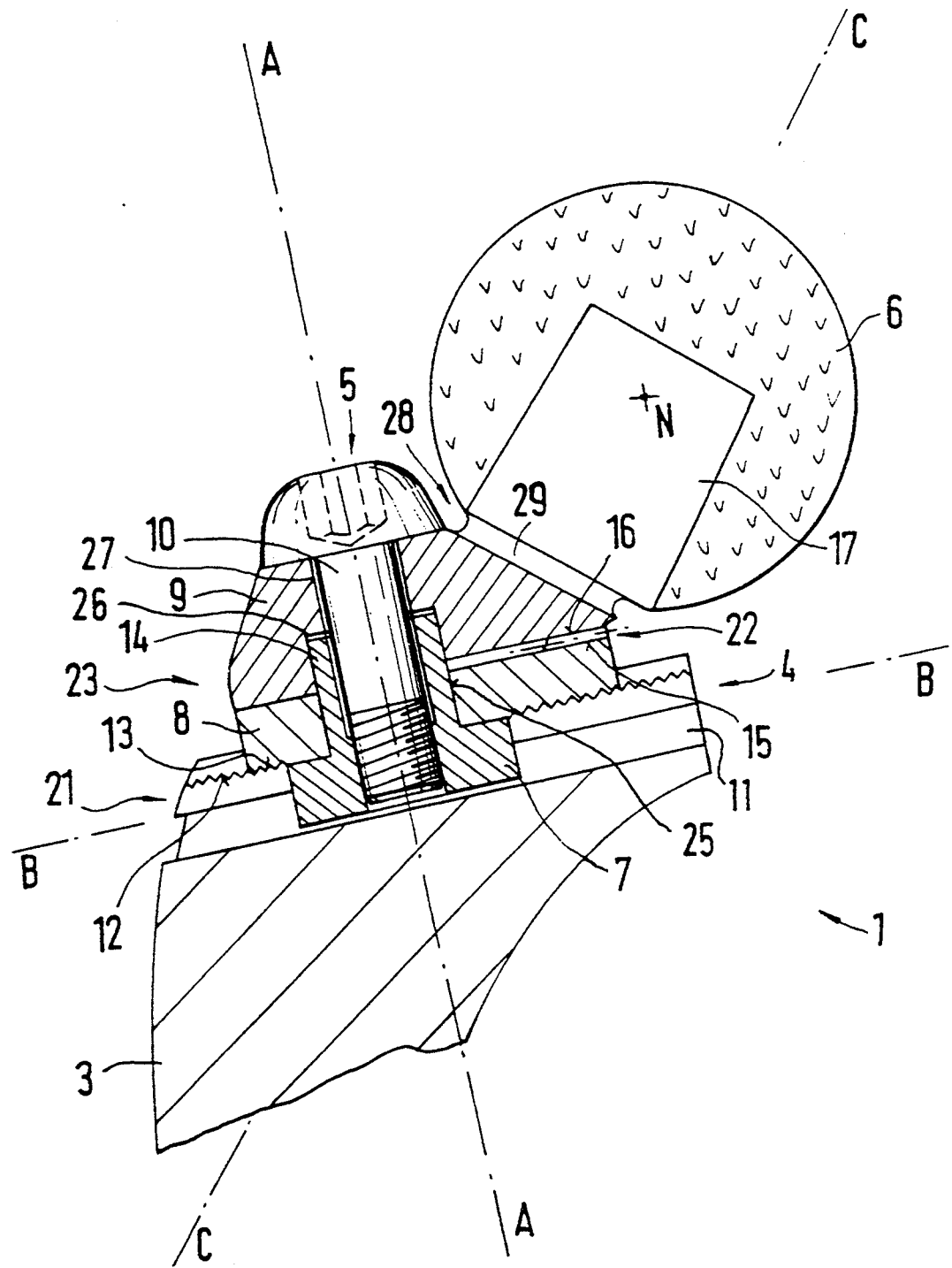

ADJUSTABLE HIP JOINT ENDOPROSTHESIS

BACKGROUND AND SUMMARY OF THE INVENTION

The present invention relates to a hip joint endoprosthesis having an adjustable prothesis head that is connected with a stem that can be fixed in the femur. The prosthesis head includes an adjusting device, which can be fixed by locking devices, and has a link element guided in a stationary link area. A supporting body of a joint head is held on the link element and is supported to be adjustable with respect to the link area via an intermediate plate. The locking devices are adjustable with respect to one another via a tension element which penetrates the adjusting device.

A hip joint endoprosthesis comprising an adjustable prosthesis head which is connected with a stem which can be fixed in the femur is shown in German Patent Application P 41 27 989.1. The prosthesis head is constructed in several pieces and is adjustable in three degrees of freedom. Toothings provide a finely graduated adjustability of a displacement in the medial-lateral direction and of a rotation around an axis perpendicularly to this direction. Securing takes place by means of a single screw which holds the meshing toothings in a tensioned state with respect to one another. The head of the joint is placed on the prosthesis head via a cone. An adjustment of the height of the head of the joint takes place by means of joint heads with cones which are pressed in deeply to different degrees and cause a displacement of the center point of the joint head in the proximal-distal direction.

An object of the invention is to provide an improved adjustable hip joint endoprosthesis which, in the case of an overload, prevents damage to the part of a hip joint endoprosthesis which is implanted in the femur.

This and other objects are achieved by the present invention which provides a stem fixable to a femur, and a prosthesis head connected to the stem. The prosthesis head includes an adjusting device, locking devices that fix the adjusting device, and a link element guided in a stationary link area. A joint head, having a supporting body, is held on the link element and is adjustable with respect to the link area via an intermediate plate. A tension element penetrates the adjusting device and fixes the locking devices with respect to one another. The prosthesis head has a force limiting device that limits to a maximum value a force to be transmitted by the hip joint endoprosthesis.

By means of the invention, a hip joint endoprosthesis is advantageously provided which, in the case of an overload, prevents damage to the part of a hip joint endoprosthesis which is implanted in the femur and, at the same time, also prevents a resulting damage to the femur.

The limiting of the forces takes place by the deformation or fracture of a material cross-section or the sliding of a frictionally engaged element in the prosthesis head. In the event of a deformation or a sliding, the prosthesis can still be used for a short period of time. As a result, a new implantation, which is connected with high risks, is avoided in each case. Instead, only that part of the prosthesis head must be exchanged which, as the force limiting device, has absorbed that portion of the force by fracture or deformation which exceeds a predetermined maximum value. When the force limiting device is constructed as a frictionally engaged element, an exchange is not even necessary but only a new adjustment for the restoring of the geometry of the hip joint endoprosthesis.

As a result of the deformation or fracture of a material cross-section or a sliding of a frictionally engaged element, an overloading is rendered clearly visible and noticeable by an extreme faulty position of the thigh.

A case of overload is characterized by the exceeding of the maximum value of the force that can be transmitted from the hip joint endoprosthesis to the femur. The maximum value of the force which can be transmitted by the force limiting device is selected in such a manner that the overload situation will not be reached, but that forces occurring in everyday life are below it. A minor exceeding of the maximum value, as may occur in exceptional situations, in the case of the material normally used for the prosthesis and an impulse-type duration of the effect, does not lead to a response of the force limiting device but is transmitted. By contrast, an exceeding of the maximum value in the event of an overload case must result in an immediate response of the force limiting device.

Other objects, advantages and novel features of the present invention will become apparent from the following detailed description of the invention when considered in conjunction with the accompanying drawings.

BRIEF DESCRIPTION OF THE DRAWINGS

The single drawing figure is a sectional view of an adjustable hip joint endoprosthesis constructed in accordance with an embodiment of the present invention.

DETAILED DESCRIPTION OF THE DRAWINGS

The only figure is a sectional view of an upper area 1 of an adjustable hip joint endoprosthesis with an adjusting device 23 in a frontal plane. The hip joint endoprosthesis comprises a stem 3, a link area 4 which is worked in here, as well as a prosthesis head 5. This prosthesis head 5 can be moved with respect to the link area 4 and carries a joint head 6. The prosthesis head comprises a link element 7, an intermediate plate 8 and a supporting body 9 with a tension element which is a threaded pin 10 in the illustrated embodiment, although other tensioning elements can be used. Between the supporting body 9 and the intermediate plate 8, on the one hand, and the link area 4 as well as the intermediate plate 8, on the other hand, locking devices 21, 22 are arranged that are formed of spur toothings 12, 13 and 15, 16. The hip joint endoprosthesis is inserted in a femur and is fixed there. The joint head 6 is in its initial position which is marked by an N.

For the adjustment of an orthopedically correct position of the joint head 6, at least three adjusting directions are provided. A first adjustment takes place by the linear displacement in the medial-lateral direction according to a line B—B; the second adjustment takes place in the proximal-distal direction according to a line C—C; and a third adjustment takes place by the rotation about an axis A—A which, viewed onto the front plane, is disposed perpendicularly on line B—B.

On its surface facing the prosthesis head 5, the link area 4 has an undercut groove 11 in the medial-lateral direction, into which the link element 7 engages. By means of this undercutting, the link element 7 can transmit tension forces originating from the threaded pin 10 perpendicularly with respect to the direction of the groove 11. On the surface of the link area 4, the first linear spur toothing 12 is arranged. Above the link area 4, the intermediate plate 8 is disposed, on the surface of which facing the link area 4, the second linear spur toothing 13 is arranged which forms the counterpart to the first linear spur toothing 12 and meshes with it. The spur toothing 12 extends along the whole length of the link area 4 and is arranged only on one side of the link area 4. On the opposite side, a prismatic guide is arranged which is not shown and which guides the prosthesis head 5 with respect to the stem 3.

A bore 25 in the intermediate plate 8 receives a pin 14 of the link element 7. Radially with respect to the center point of this bore 25 and opposite the second linear spur toothing 13 on the top side of the intermediate plate 8, the first radial spur toothing 15 of the locking device 22 is arranged in a raised manner and is bounded by an approximately circular-segment-shaped area.

The supporting body 9 rests on the intermediate plate 8, the pin 14 of the link element 7 projecting into a pocket bore 26 of the supporting body 9. As an extension of this bore 26, a bore 27 is provided which has a smaller diameter and through which the threaded pin 10 is screwed through the supporting body 9 into an internal thread in the pin 14 of the link element 7. On the opposite side and corresponding to the first radial spur toothing 15, the supporting body 9 has a second radial spur toothing 16. A circular-segment-shaped area which bounds this spur toothing 16 comprises a smaller angle than the area bounding the first radial spur toothing 15.

The supporting body 9 is provided with a shaft which has an external cone 17 on its end. The joint head 6, into which a corresponding internal cone is machined, is placed on this external cone 17. As the force limiting device 28, a surrounding notch 29 is provided between the shaft and the external cone 17. With respect to its shape and depth, the force limiting device 28 is designed such that, in the material cross-section bounded by the notch 29, the strength of the material is exhausted slightly earlier than in all other material cross-sections situated in the flux of force from the joint head 6 to the stem 3. In other words, a predetermined breaking point is provided here in the supporting body 9.

The strength of the material is preferably selected such that every stress is transmitted in a secure and fatigue-proof manner. Short loads exceeding the strength of the material, such as the steel types normally used for prosthesis, do not immediately result in a fracture and are therefore still transmitted. Only stresses of a fairly long duration or stresses which are clearly above this magnitude result in an immediate fracture in the material cross-section bounded by the notch 28.

After the fracture, a force transmission by way of the hip joint endoprosthesis is no longer possible. However, only the damaged supporting body 9 must be exchanged by surgery while, particularly the stem 3 anchored in the femur and the femur itself are not affected detrimentally.

In a further embodiment of the invention, which is not shown, it is advantageously provided that overloading does not result in a fracture but in deformations. This may take place, for example, by designing the shaft of the supporting body 9 in the case of a pressure load as a hollow profile or, in the case of a bending load, as a bending bar. After the overloading, a force transmission by way of the hip joint endoprosthesis will still be possible although the changes which occurred as a result of the deformation require that the supporting body 9 be exchanged soon.

The force limiting device 28 may, for example, be constructed as a frictionally engaging element. This element absorbs force peaks, which exceed the frictional force, by means of sliding. As a result, the prosthesis geometry is changed which must then be reestablished by means of a new adjustment.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A hip joint endoprosthesis comprising:
   a stem fixable to a femur;
   a prosthesis head connected to the stem, the prosthesis head including an adjusting device, locking devices coupled to the adjusting device that fix the adjusting device, a stationary link area coupled to at least one of the locking devices and a link element guided in the stationary link area;
   an intermediate plate on the stationary link area;
   a joint head, having a supporting body, which is held on the link element and the intermediate plate and is adjustable in a medial lateral direction with respect to the link area through the intermediate plate;
   a tension element which penetrates the adjusting device and fixes the locking devices with respect to one another; and
   a force limiting device in the prosthesis head, said force limiting device limiting to a maximum value a force to be transmitted by the hip joint endoprosthesis, wherein at least one of the stationary link area, the adjusting devices, the link element, the locking devices, the intermediate plate and the tension element have material cross-sections situated so as to be in a flux of force from the joint head to the stem, and wherein the force limiting device has a material cross-section with a strength of material that is exhausted earlier than all other material cross-sections situated in the flux of force from the joint head to the stem.

2. A hip joint endoprosthesis according to claim 1, wherein the force limiting device comprises a reduced material cross-section of the prosthesis head which forms a predetermined breaking point when the maximum value of the force is reached.

3. A hip joint endoprosthesis according to claim 1, wherein the force limiting device comprises a reduced material cross-section of the prosthesis head which forms a desired-deformation point when the maximum value of force is reached.

4. A hip joint endoprosthesis according to claim 1, wherein the force limiting device is provided between the prosthesis head and a cone and consists of a notch.

5. A hip joint endoprosthesis comprising:
   a stem;
   an adjustable prosthesis head which is connected with the stem;
   a link area having an undercut groove extending in a direction of a medial-lateral displacement and provided with a first linear spur toothing on a surface and perpendicularly to said groove;

a link element guided in the groove, having cylindrical pin that has a bore with an internal thread;

an intermediate plate resting on the link area, a bore receiving the cylindrical pin, and a second linear spur toothing meshing with the first spur toothing of the link area;

a first radial spur toothing opposite the second spur toothing, the first radial spur toothing being on the top side of the plate radially with respect to the center point of the bore and is bounded by a circular-segment-shaped area;

a supporting body that rests on the intermediate plate, a pocket bore receiving the cylindrical pin of the link element and a second radial spur toothing being arranged on the supporting body in such a manner that it meshes with the first radial spur toothing of the plate, and a shaft projecting diagonally radially with respect to the bore carrying a cone for receiving a joint head, the joint head being provided with a conical recess corresponding to the cone, a pressing-in depth of this conical recess being pre-set by manufacture;

a single threaded pin, by means of a bore in the supporting body which extends approximately perpendicularly with respect to the direction of the medial-lateral displacement, is connected with the internal thread of the pin and, in a tensioned state, holds the link area, the intermediate plate and the supporting body and also the meshing locking devices in tension with respect to one another; and a force limiting device provided on a diagonally radially projecting shaft on a starting piece of the cone of the supporting body, the force limiting device comprising a surrounding notch which, when a maximum force is reached which is below the maximum forces of all other elements, allows the shaft to be separated from the cone.

* * * * *